(12) United States Patent
Okuchi et al.

(10) Patent No.: US 6,700,603 B1
(45) Date of Patent: Mar. 2, 2004

(54) INSPECTION SYSTEM FOR INSPECTING DISCRETE WIRING PATTERNS FORMED ON A CONTINUOUS SUBSTRATE SHEET OF A FLEXIBLE MATERIAL

(75) Inventors: Tetsuya Okuchi, Kawanishi (JP); Hiroyuki Ishiguro, Koriyama (JP); Yoshio Mori, Yawata (JP); Takeshi Kitamura, Koriyama (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 09/486,698
(22) PCT Filed: Jul. 28, 1999
(86) PCT No.: PCT/JP99/04040
§ 371 (c)(1),
(2), (4) Date: Mar. 3, 2000
(87) PCT Pub. No.: WO00/07031
PCT Pub. Date: Feb. 10, 2000

(30) Foreign Application Priority Data

Jul. 28, 1998 (JP) .......................................... 10-213307
Jul. 28, 1998 (JP) .......................................... 10-213308
Feb. 23, 1999 (JP) .......................................... 11-044050

(51) Int. Cl.[7] ................................................ H04N 7/18
(52) U.S. Cl. ....................................... 348/126; 348/129
(58) Field of Search ........................... 348/125, 87, 88, 348/92, 94, 126, 129; H04N 7/18

(56) References Cited

FOREIGN PATENT DOCUMENTS

| EP | 63163150 | 7/1988 |
|---|---|---|
| EP | 63246642 | 10/1988 |
| EP | 0122970 | 9/1989 |
| EP | 01229947 | 9/1989 |
| EP | 02067948 | 3/1990 |
| EP | 0443106 A2 | 8/1991 |
| JP | 63-163150 | 7/1988 |
| JP | 63-246642 | 10/1988 |
| JP | 1-227970 | 9/1989 |
| JP | 1-229947 | 9/1989 |
| JP | 2-67948 | 3/1990 |

*Primary Examiner*—Young Lee
(74) *Attorney, Agent, or Firm*—Rader Fishman & Grauer, PLLC

(57) ABSTRACT

An inspection system for inspecting discrete wiring patterns on a continuous substrate sheet of a flexible material by making the use of the substrate sheet as a feeding carrier. The system is capable of assuring accurate positioning of the wiring patterns (14) for reliable inspection even with the use of the flexible substrate sheet (10) as the sole feeding carrier. The inspection system includes an inspection zone (30) provided with camera (51, 54) for inspecting the individual wiring patterns (14) and detecting a position of said wiring pattern on the substrate sheet. A draw-in roller (31, 32) is provided to introduce the substrate into the inspection zone. Associated with the draw-in roller is a draw-out roller (32, 33) which draws out the substrate sheet from the inspection zone and is positioned to define the inspection zone between the draw-in roller and the draw-out roller as well as to give a tension to the substrate sheet for extending the substrate sheet straight through the inspection zone. A controller (60) is provided to control a position of the substrate sheet passing through the inspection zone based upon a position signal detected by the camera as indicative of the position of the individual wiring patterns on the substrate sheet within the inspection zone. Thus, the wiring pattern can be exactly positioned within the inspection zone relative to the camera for reliable inspection thereby.

10 Claims, 8 Drawing Sheets

INSPECTION SYSTEM FOR INSPECTING DISCRETE WIRING PATTERNS FORMED ON A CONTINUOUS SUBSTRATE SHEET OF A FLEXIBLE MATERIAL

TECHNICAL FIELD

The present invention is directed to an inspection system for inspecting discrete wiring patterns formed on a continuous substrate sheet of a flexible material, and more particularly to such inspection system capable of feeding the wiring patterns for inspection by use of the substrate sheet as a feeding carrier or conveyer.

BACKGROUND ART

In the manufacture of the printed boards, it has been a quite common to form a number of identical wiring patterns on a continuous substrate sheet of a relatively flexible material and then to cut the substrates into the discrete circuit boards each having the wiring pattern for an end use. For inspection of the wiring patterns of the circuit boards, it has been proposed to place the discrete circuit boards one by one on a suitable conveyer for feeding the boards into an inspection zone where they are successively scanned for inspection of the wiring pattern. However, this inspection system suffers from a problem in that the boards must be accurately located on the conveyer for exact registration with the camera in the inspection zone, and that the system necessitates the conveyer.

SUMMARY OF THE INVENTION

The present invention has been achieved in view of the above problem and provides an advantageous system for inspecting discrete wiring patterns on a continuous substrate sheet of a flexible material by making the use of the substrate sheet as a feeding carrier. Therefore, a main object of the present invention is to provide the inspection system capable of using the substrate sheet as the feeding carrier and of assuring accurate positioning of the wiring patterns for reliable inspection even with the use of the flexible substrate sheet as the sole feeding carrier. The inspection system in accordance with the present invention includes an inspection zone provided with camera means for inspecting the individual wiring patterns and detecting a position of said wiring pattern on the substrate sheet. A draw-in roller is provided to introduce the substrate into the inspection zone. Associated with the draw-in roller is a draw-out roller which draws out the substrate sheet from the inspection zone and is positioned to define the inspection zone between the draw-in roller and the draw-out roller as well as to give a tension to the substrate sheet for extending the substrate sheet straight through the inspection zone. A control means is provided to control a position of the substrate sheet passing through the inspection zone based upon a position signal detected by the camera means as indicative of the position of the individual wiring patterns on the substrate sheet within the inspection zone. Thus, the wiring pattern can be exactly positioned within the inspection zone relative to the camera means for reliable inspection thereby.

Since the wiring patterns can be formed on the substrate sheet at a regular precise interval, the exact positioning of the wiring pattern in the inspection zone is made to compensate for a possible lateral shift of the substrate sheet being fed and for a possible angular directional divergence of the substrate sheet from an intended feed direction. In order to compensate for such undesired erroneous movement of the substrate sheet during the feed, the present invention is contemplated to utilize a feeder of feeding the substrate sheet into the inspection zone and a collector of collecting the substrate sheet as constituting an exact positioning mechanism. The mechanism allows the draw-in roller as well as the draw-out roller to shift in a direction transverse to the feeding direction. The control means operates, in response to the position signal, to shift at least one of the draw-in roller and the draw-out roller for correct positioning of the wiring pattern within the inspection zone.

The present invention discloses various modes of feeding the substrate sheet for reliable inspection of the wiring patterns, and specific features in association with the individual modes. For all modes, the camera means is composed of an inspection camera means and a position camera means. The inspection camera means provides a scanned image of the wiring pattern to an image inspector where the scanned image is compared with a reference image for determination of a defect in the wiring pattern. The position camera means detects marks on the substrate sheet to acknowledge a pre-inspection position of the wiring pattern which is just before being inspected by the inspection camera and provides the position signal indicative of the pre-inspection position.

In a first mode, the substrate sheet is fed at a uniform speed and the inspection camera means is composed of an array of inspection cameras arranged in a direction transverse to a feeding direction of the substrate sheet in such a manner to cover a whole width of the wiring patterns. A speed sensor is provided to detect the feeding speed of the substrate sheet and to provide a speed signal indicative of the feeding speed. The control means is responsive to the speed signal to feed the substrate sheet at the uniform speed. Further, based upon the position signal as well as the speed signal, the control means activates the inspection camera means for scanning the image of the wiring pattern in synchronism with the position of the wiring pattern.

In a second mode, the inspection camera means comprises an array of inspection cameras arranged in an array direction transverse to a feeding direction of the substrate sheet so as to cover the whole width of the wiring pattern when the array is shifted between a first position and a second position in the array direction. The control means operates to feed the substrate sheet forwardly along the feeding direction by one forward step during which the inspection camera means at the first position completes scanning of a portion of the wiring pattern, and subsequently to feed the substrate sheet reversely by one reverse step during which the inspection camera means at the second position completes scanning of the rest of the wiring pattern.

In a third mode, the control means operates to feed the substrate sheet intermittently such that the wiring pattern is held stationary at an inspection position for a predetermined period during which the inspection camera means is controlled to move relative to the wiring pattern for inspection of the wiring pattern.

In a fourth mode, the inspection camera means comprises an array of inspection cameras arranged in a direction parallel to a feeding direction of the substrate sheet so as to cover the whole width of the wiring pattern when the array reciprocates by one cycle along a transverse direction perpendicular to the feeding direction. The control means operates to hold the substrate sheet at a first inspection position where the inspection camera means is shifted by half of the one cycle in the transverse direction in order to scan a portion of the wiring pattern, and subsequently feed the substrate sheet by one step to a second inspection position where the inspection camera is shifted by the remaining half of the one cycle in the transverse direction in order to scan the rest of the wiring pattern. In this way, the control means operate to feed the substrate sheet intermittently so that the wiring pattern is held stationary at the first and second inspection positions at which the inspection camera means is controlled to move relative to the wiring pattern for inspection of the wiring pattern.

For the second, third, and fourth modes where the substrate sheet is held stationary or fed stepwise during the inspection of the wiring pattern by the inspection camera means, it is advantageous to provide a suction table behind the substrate sheet so as to hold the substrate sheet flat on the suction table for facilitating the inspection. The suction table may be movable in synchronism with the substrate sheet being fed step-wise during the inspection. Further, the suction table may be utilized to effect correct positioning of the wiring pattern in relation to the inspection camera means based on the position signal from the position camera means. For this purpose, the suction table is disposed to have its feed axis extending along a feeding direction of the substrate sheet and is capable of swinging around a vertical axis perpendicular to a plane of the substrate sheet so as to adjust an angle of the feed axis with respect to the feeding direction, thereby compensating for an angular divergence of the substrate from an intended feed direction.

These and still other objects and advantageous features of the present invention will become more apparent from the following description of the preferred embodiments when taken in conjunction with the attached drawings.

DETAILED DESCRIPTION OF THE EMBODIMENTS

First Embodiment FIGS. 1 to 6

Figure 1:
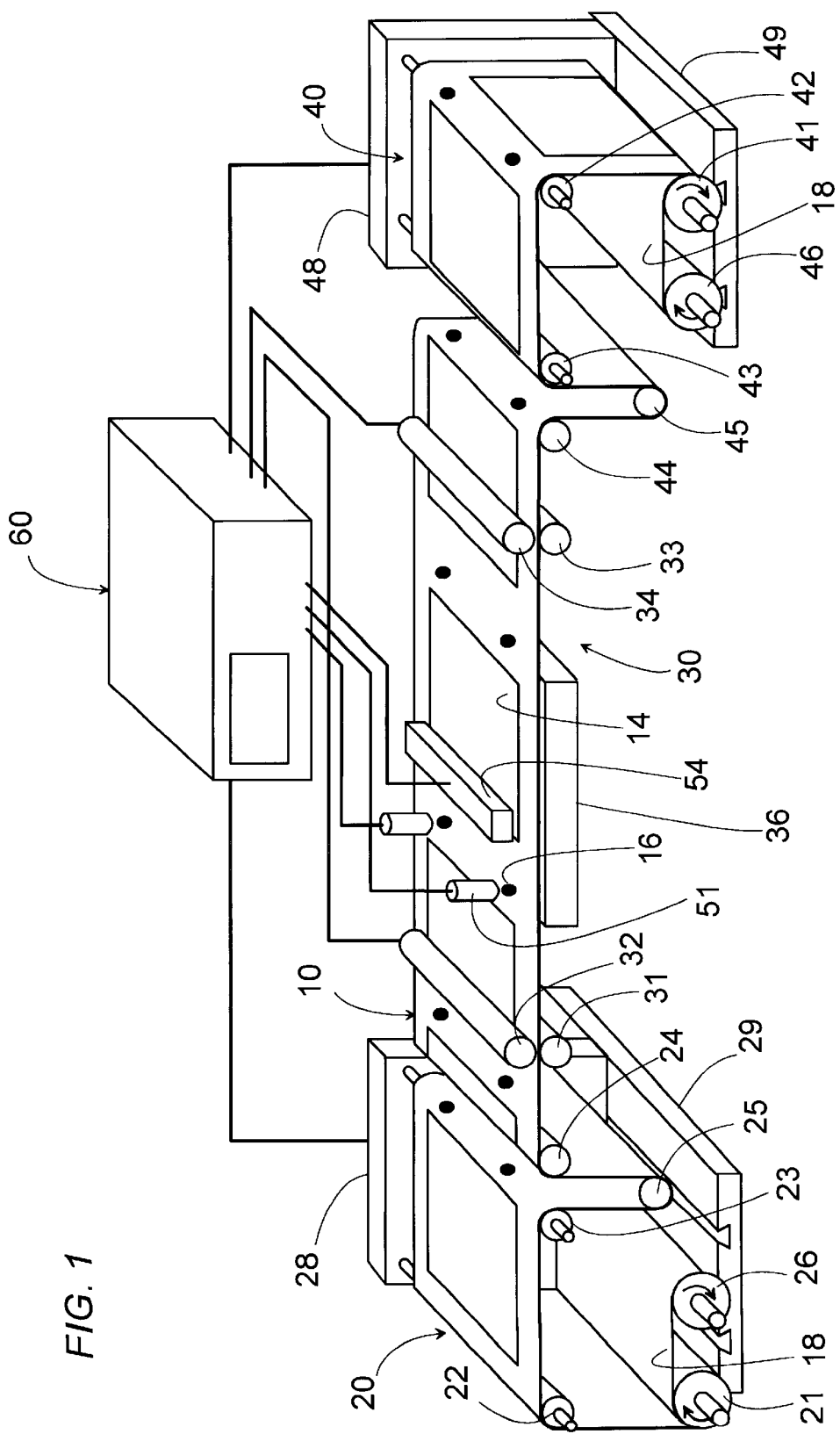
FIG. 1 is a perspective view of an inspection system in accordance with a first embodiment of the present invention.
Figure 3:
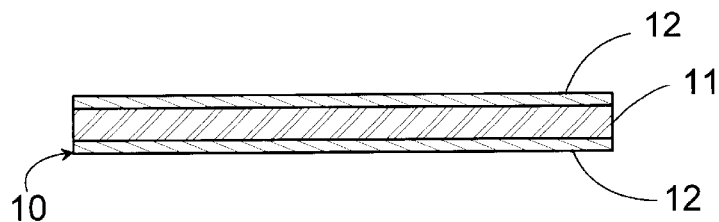
FIG. 3 is a sectional view of a substrate sheet on which a number of wiring patterns are formed.
Figure 4:
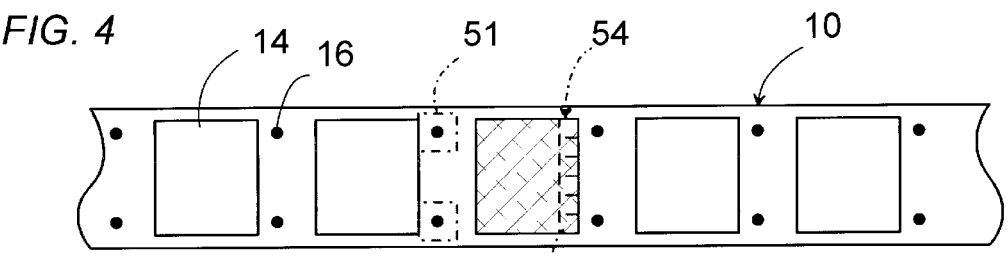
FIG. 4 is a plan view of the substrate sheet with the wiring patterns to be inspected.
Figure 5:
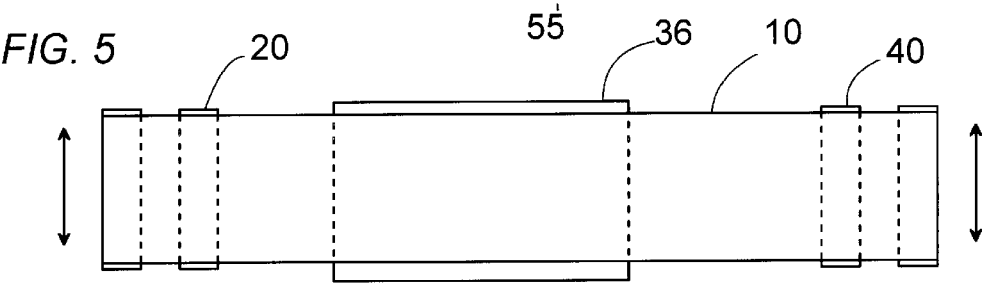
FIG. 5 is a schematic top view of the system.

Referring now to FIG. 1, there is shown an inspection system in accordance with a first embodiment of the present invention. The system is provided to inspect discrete wiring patterns formed on a continuous substrate sheet of a flexible material. For example, as shown in FIG. 3, the substrate sheet 10 is a laminate composed of a 0.04 mm to 0.2 mm thick resin-impregnated glass-sheet 11 and two outer 35 $\mu$m thick copper layers 12. The wiring patterns 14 are formed on the upper copper layer 12 by etching. The wiring patterns to be inspected by the present system may be otherwise those of a resist material deposited on the copper layer. The substrate sheet 10 are formed adjacent to the individual wiring patterns 14 with plural sets of position markings 16, each set having two dot markings 16 arranged transversely of a length of the substrate sheet 10, as shown in FIG. 4. The markings 16 are printed together with the wiring patterns 14 on the substrate 10 at precise locations and can be therefore utilized as calibrations for the substrate sheet.

The system includes a feeder 20, a collector 40, and an inspection zone 30 provided therebetween. The feeder 20 includes a unwinder 21 of unwinding a roll of the substrate sheet 10, feed rollers 22, 23, 24, and a dancer roller 25. A recovery roller 26 is provided adjacent to the unwinder 21 to recover a protective film 18 from the underside of the substrate sheet 10. The substrate sheet 10 from the feeder 20 is introduced into the inspection zone 30 by means of a draw-in roller composed of a driving roller 31 and a pinch roller 32, and is guided into the collector 40 by a draw-out roller composed of a driving roller 33 and a pinch roller 34. The collector 40 includes a winder 41 of winding the substrate sheet, feed rollers 42, 43, 44, and a dancer roller 45. A supply roller 46 is provided adjacent to the winder 41 to supply a like protective film on the underside of the substrate being wound on the winder 41. The draw-in roller and the draw-out roller are so positioned to define therebetween the inspection zone 30 and to give a tension of extending the substrate sheet 10 horizontally in the inspection zone 30. A guide table 36 is juxtaposed below the substrate sheet 10 in the inspection zone for guiding the substrate sheet flat on the table 35. The feeder 20 as well as the collector 40 are both made movable in a direction transverse to the feeding direction of the substrate sheet in order to make a fine adjustment of a transverse position of the substrate sheet as well as a feeding direction. For this purpose, the feeder 20 is carried by a frame 28 which is movably supported to a fixed base 29 to allow the transverse movement of the feeder 20. Likewise, the collector 40 is carried by a frame 48 which is movably supported to a fixed base 49 to allow the transverse movement of the collector 40.

Figure 2:
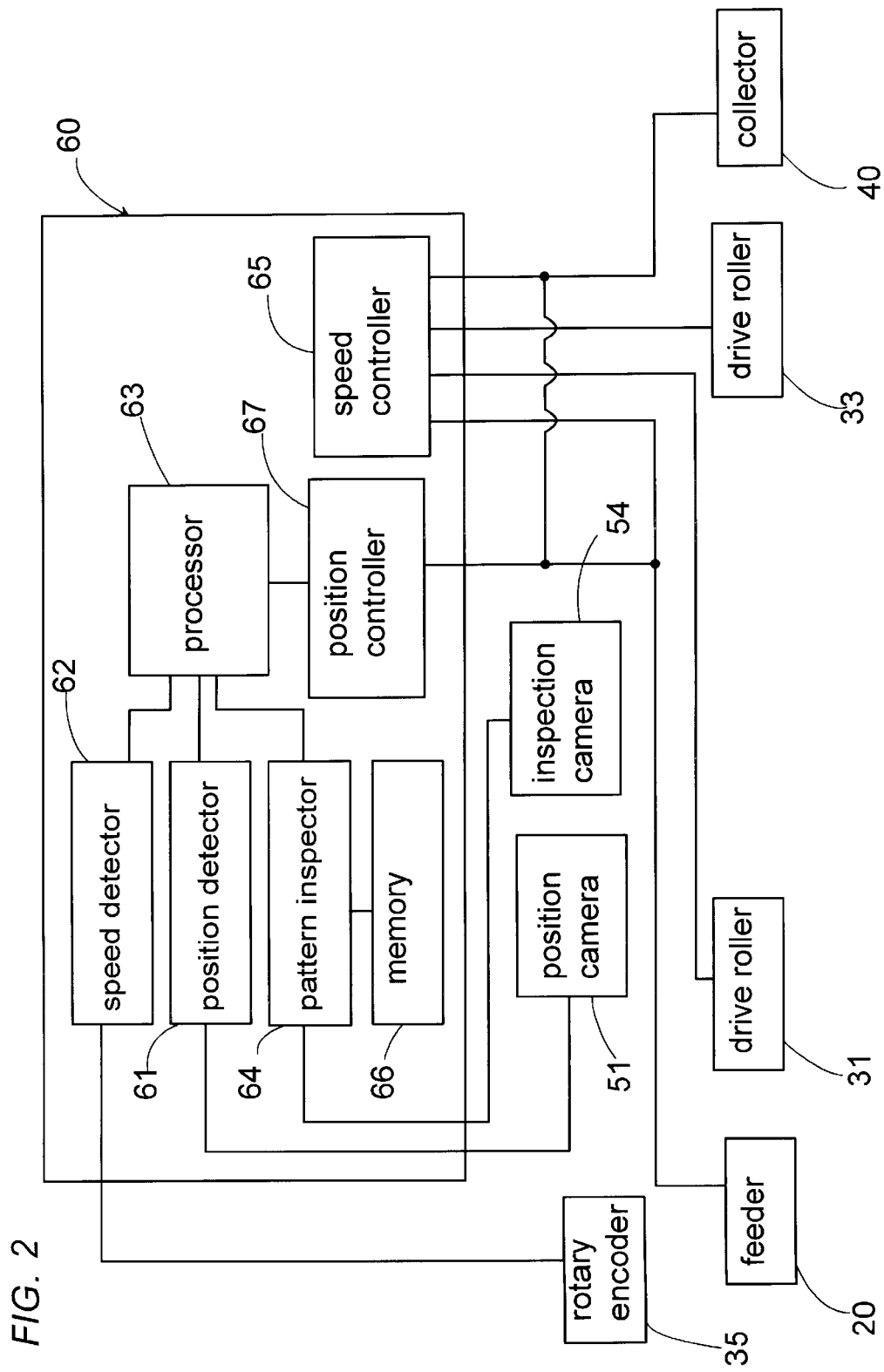
FIG. 2 is a block diagram of the inspection system.

The inspection zone 30 is provided with a pair of position cameras 51 for monitoring the position markings 16 and an inspection camera 54 for scanning the wiring patterns 14. The inspection camera 54 includes an array of camera units 55 arranged closely in a transverse array perpendicular to the feeding direction of the substrate sheet 10 in such a manner that the entire wiring pattern 14 is scanned while the substrate sheet 10 is fed in the forward direction with the camera units being held stationary. The cameras 51 and 54 are connected to a controller 60 for controlled operations of detecting the position of the wiring patterns and scanning the same. The controller 60 also controls the speed of feeding the substrate sheet 10, i.e., the rotating speed of the drive rollers 31 and 33, in addition to the operations of the feeder 20 and the collector 40 including the transverse movement thereof. In this embodiment, the controller 60 acts to feed the substrate sheet 10 at a uniform speed through the inspection zone 30. A rotary encoder 35 is provided on a shaft of the pinch roller 32 to detect the speed which is acknowledged by the controller 60 for a feed back control of maintaining the feed speed constant. For these purposes, the controller 60 includes, as shown in FIG. 2, a position detector 61 connected to receive the monitored data from the position camera 51, a pattern inspector 64 connected to receive the scanned image of the wiring pattern 14 from the inspection camera 54, a speed detector 62 for detection of the feeding speed. An output of the speed detector 62 is fed to processor 63 which in turn activates a speed controller 65 for controlling the speeds of the unwinder 21, drive rollers 31 and 33, and winder 41 in order to keep the feed speed constant. The pattern inspector 64 compares the scanned image of the wiring pattern with a reference image representative of a correct wiring pattern to determine whether the wiring pattern being scanned is defective or not. If the wiring pattern is determined defective, the pattern inspector 64 stores an identification number assigned to this particular wiring pattern into a memory 66 such that the defective wiring pattern could be re-examined or rejected thereafter by reference to the identification number. The identification number may be printed on the substrate sheet so as to be acknowledged by the image inspector or may be acknowledged by counting the individual wiring patterns being inspected.

Figure 6:
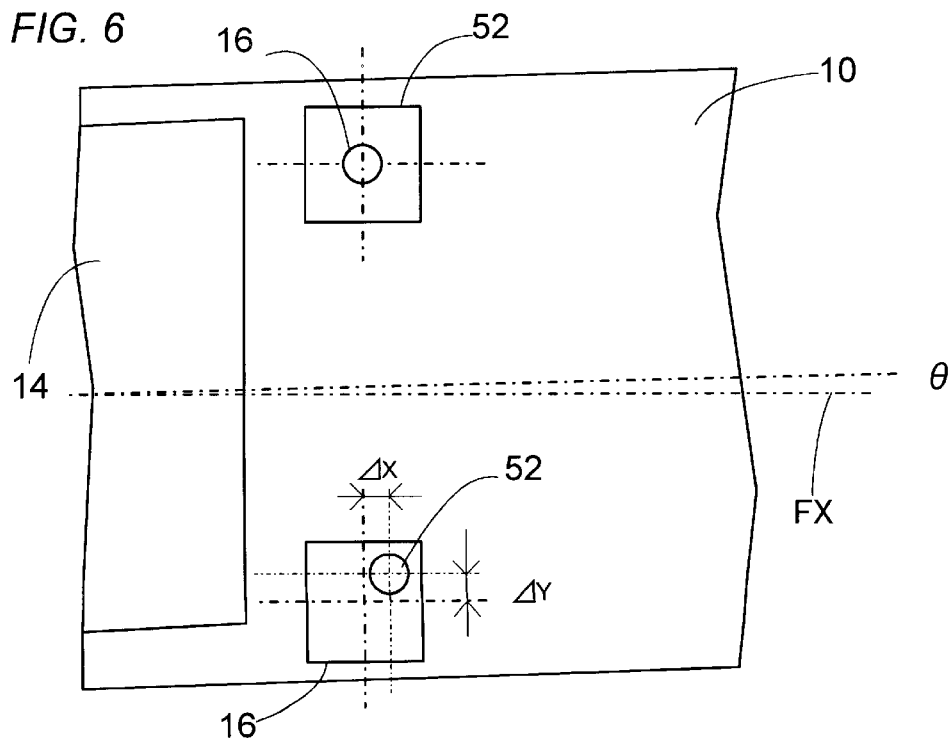
FIG. 6 is a partial view of the substrate for explaining an operation of correcting the position of the wiring pattern.

The position camera 51 detects a pre-inspection position of the wiring pattern 14 which is just before being inspected by the inspection camera 54 and provides a position signal indicative of the pre-inspection position to the position detector 61 where it is analyzed to give an error with respect to a correct feeding axis. The error includes a transverse displacement error and an angular divergence error of the wiring pattern in the pre-inspection position in relation the correct feeding axis. Such error is evaluated in the processor 63 to give a compensation signal to a position controller 67 which responds to make the transverse movement of the feeder 20 and/or the collector 40 in such a manner as to eliminate the error, thereby placing the wiring pattern into a correct position for inspection by the array of the inspection camera 54. Details of the operation are explained with reference to FIG. 6. Each of the position cameras 51 has a field of view 52 with center X-axis and Y-axis. When the wiring pattern 14 in the pre-inspection position is inclined with respect to the correct feeding axis, as shown in the figure, or shifted laterally, the corresponding markings 16 captured respectively in the field of views 52 of the individual position cameras 51 show deviations ΔX and/or ΔY with reference to the center X-axis and Y-axis. Such deviations represent the angular divergence error or the transverse displacement error of the wiring pattern. FIG. 6 demonstrates undesired angular divergence θ of the wiring pattern 14 with respect to the feeding axis FX. Based upon ΔX and ΔY being obtained, the processor 63 generates the compensation signal for eliminating the error before the wiring pattern 14 is fed into a position of being inspected the inspection camera 54.

Second Embodiment FIGS. 7A to 7E

Figure 7A:
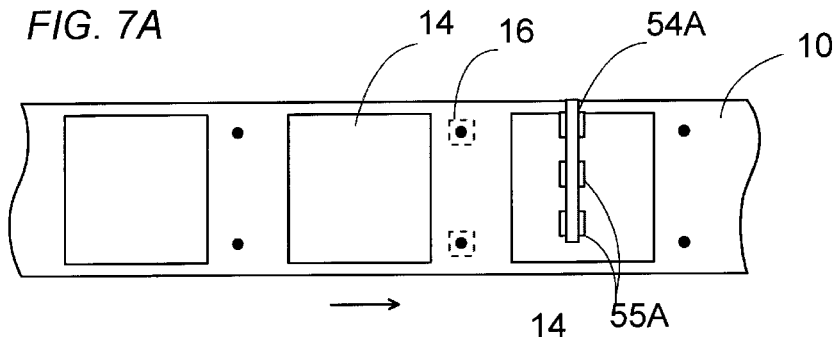
FIGS. 7A to 7E are views for explaining the operation of an inspection system in accordance with a second embodiment of the present invention.
Figure 7B:
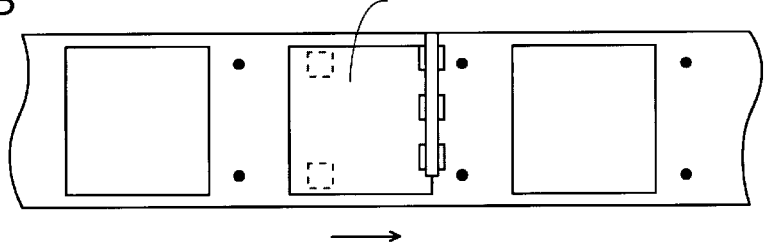
Figure 7C:
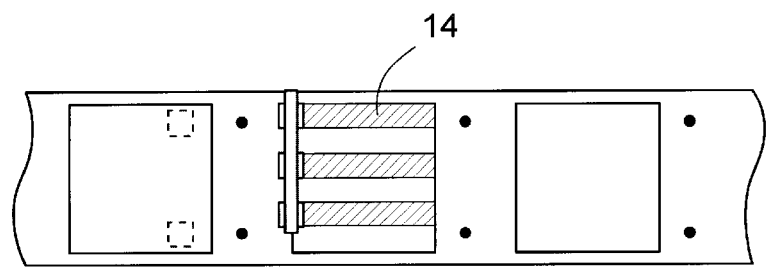
Figure 7D:
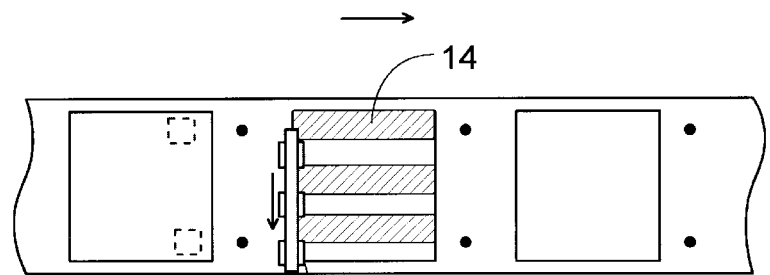
Figure 7E:
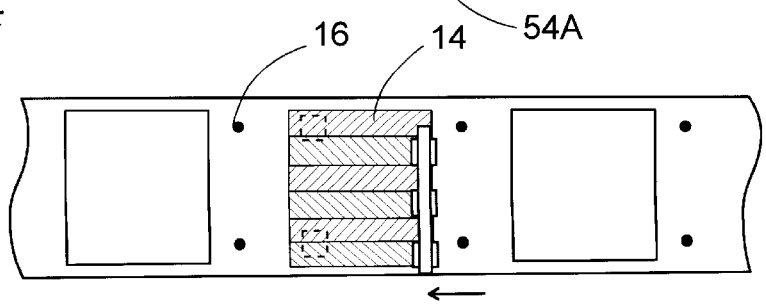

FIGS. 7A to 7E illustrates an inspection system in accordance with a second embodiment of the present invention which is similar in construction with the first embodiment except that an inspection camera 54A is composed of separate camera units 55A spaced along the transverse direction of the substrate sheet 10 and is movable in the transverse direction between a first position of FIGS. 7A to 7C and a second position of FIGS. 7D and 7E. Like parts are designated by like numerals with a suffix letter of 'A'. The camera units 55A are spaced by a fixed distance such that the entire width of the wiring pattern 14 is covered when the units are shifted by the distance between the first and second positions. With the use of the inspection camera 54A of this structure, a control is made to feed the substrate sheet 10 in forward and reverse directions. Operation of the system is now discussed. As shown in FIG. 7A, when the wiring pattern 14 proceeds to a pre-inspection position where the corresponding position markings 16 are captured by the position cameras 51A, the controller operates to feed the substrate sheet 10 at a relatively high speed to a first inspection position of FIG. 7B where the leading edge of the wiring pattern 14 is aligned with the inspection camera 54A. Then, the controller feeds the substrate sheet 10 at a relatively low speed by one forward step to a second inspection position of FIG. 7C with the inspection camera 54A held at the first position, during which a half area of the wiring pattern (as indicated by hatched lines) is scanned. Then, the inspection camera 54A is moved in the transverse direction to the second position, as shown in FIG. 7D. Subsequently, the substrate sheet 10 is fed by one reverse step at the relatively low speed to a position of FIG. 7E, during which the remainder half of the wiring pattern 14 is scanned. Thus, the entire area of the wiring pattern is scanned by feeding the substrate sheet 10 forwardly and then reversely by the same step. Thereafter, the substrate sheet 10 is fed forwardly at the high speed to a position of FIG. 7A for inspection of the next wiring pattern.

It is noted that the position cameras 51A act also in this embodiment to detect the pre-inspection position of the wiring pattern 14 using the position markings 16 in order to achieve correct positioning of the wiring pattern at the first inspection position of FIG. 7B in the same manner as made in the first embodiment. Further, it is noted in this connection that the controller acknowledges the pre-inspection position of the wiring pattern 14 when the position markings 16 come into the fields of the view of the corresponding position cameras 51A even if each marking 16 is not strictly coincident with the longitudinal center of the field of view of the camera, i.e., the Y-axis as shown in FIG. 6. Then, the controller operates to feed the substrate sheet 10 by a fixed distance at a rapid speed and to feed it by a suitable distance at a low speed for effecting a fine adjustment of the wiring pattern to the correct position of FIG. 7B in consideration of the deviation ΔX. With this scheme, it is possible to make a reliable inspection of each wiring pattern while reducing a run time of consecutively inspecting the individual wiring patterns.

Figure 8A:
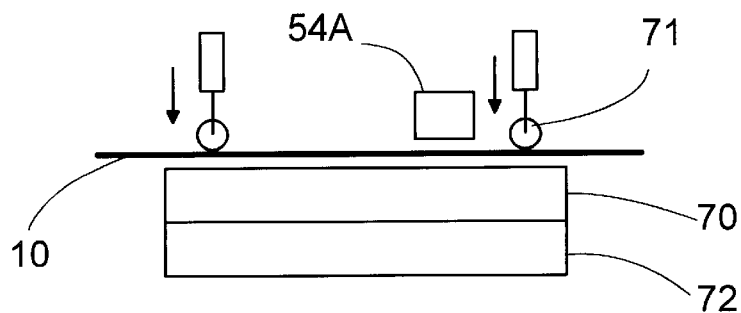
FIGS. 8A and 8B are schematic views for explaining an operation of a suction table applicable to the above embodiment.
Figure 8B:
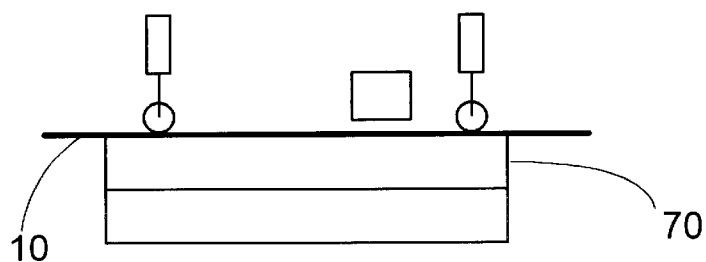
Figure 9A:
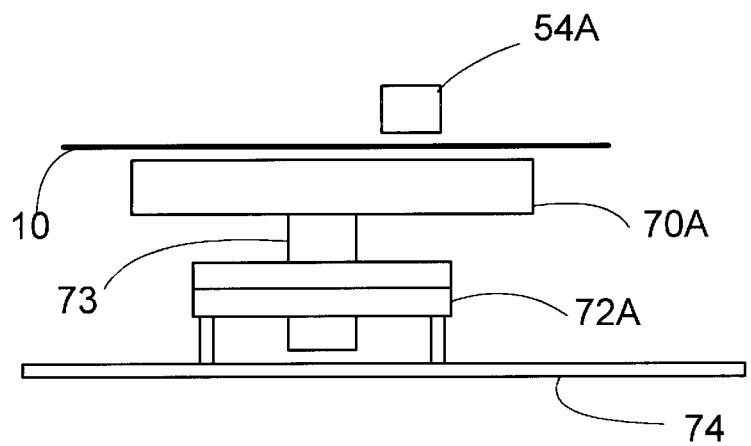
FIGS. 9A and 9B are schematic views for explaining an operation of another suction table also applicable to the above embodiment.
Figure 9B:
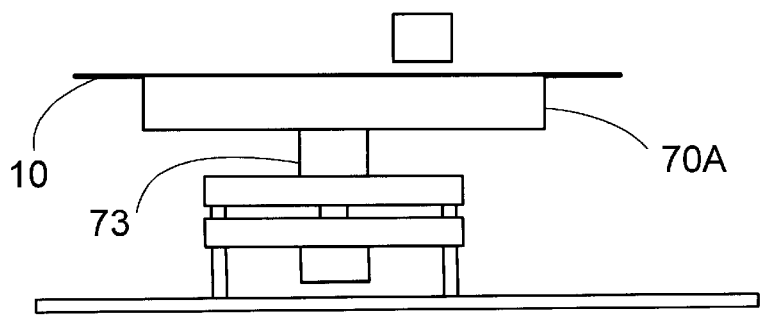

As shown in FIGS. 8A and 8B, it is preferred In this embodiment to dispose a suction table 70 behind the substrate sheet 10 in the inspection zone for holding the substrate sheet by a suction force while the wiring pattern is scanned by the inspection camera 54A. In order to assist holding the substrate sheet 10 flat against the suction table 70, there may be utilized press-rollers 71 which are controlled to press the sheet against the table 70 when the wiring pattern comes into the position of being scanned, after which the sheet is held by the suction force on the table for reliable scanning of the wiring pattern. The table 70 is supported on a base frame 72 to be movable for a limited length along the feeding direction so that the substrate sheet 10 can move for inspection by the inspection camera, i.e., between the positions of FIGS. 7B to 7E, while being held against the table 70. Further, as shown in FIGS. 9A and 9B, a vertically movable suction table 70A may be utilized for holding the substrate sheet thereon when the wiring pattern is in the position of being scanned and for releasing the substrate sheet while the sheet is fed from the pre-inspection position to the inspection position. The suction table 70A is pivotally supported to a base frame 72A through a cylinder 73 so as to be pivotable about a vertical axis of the cylinder. With this pivotable structure, the table 70A can act to compensate for the angular divergence error detected by the position camera for correct positioning of the wiring pattern in relation to the inspection camera. The table 70A is also movable along the feeding direction of the substrate sheet with the base frame 72A supported movably on a guide rail 74, in order to follow the movement of the substrate sheet during the inspection of the wiring pattern. In this connection, the table 70A as well as table 70 of FIG. 8A may be movable in the transverse direction in order to compensate for the transverse displacement error based upon the position signal from the position camera, as discussed with reference to the first embodiment.

Figure 10:
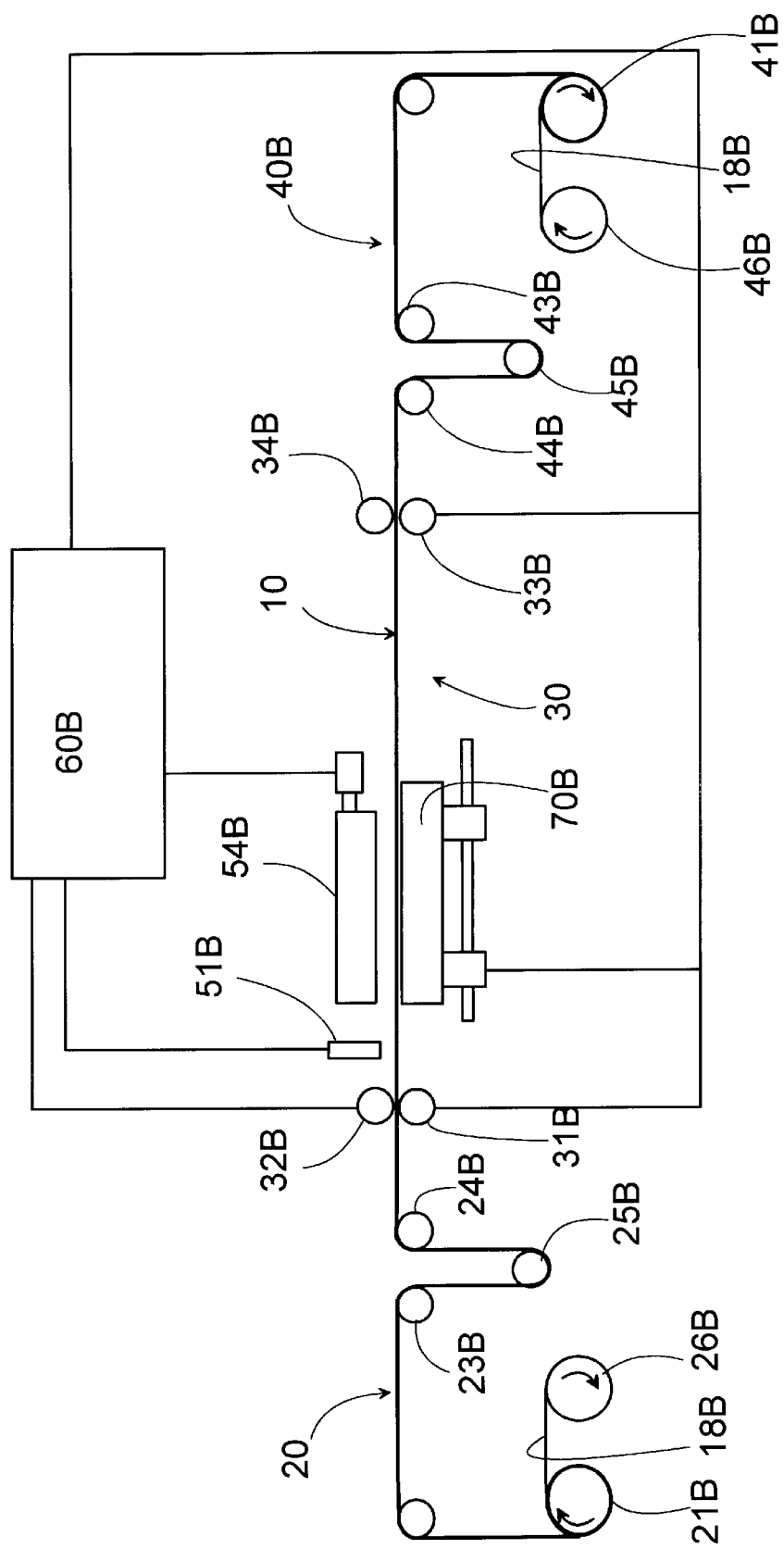
FIG. 10 is a schematic view of an inspection system in accordance with a third embodiment of the present invention.

Third Embodiment FIG. 10

Referring to FIG. 10, there is shown an inspection system in accordance with a third embodiment of the present invention which is similar to the first embodiment except that an inspection camera 54B extends along the feeding direction of the substrate sheet 10 and is movable in the transverse direction. Like parts are designated by the like reference numerals with a suffix letter of 'B'. The inspection camera 54B is composed of an array of camera units arranged closely along the feeding direction such that the entire area of the wiring pattern can be scanned when the inspection camera is shifted in the transverse direction with the substrate sheet being kept stationary. With the use of the inspection camera 54B of this structure, a controller 60B operates to feed the substrate sheet 10 intermittently for providing a standstill period during which the wiring pattern is scanned for inspection. Also in this embodiment, a like position camera 51B provides a position signal indicative of the error of the above kind for the wiring pattern at the pre-inspection position so that the controller responds to compensate for the error when the wiring pattern is fed to the inspection position of being scanned by the inspection camera, by shifting the feeder 20A and/or the collector 40A. A like suction table 70B as utilized in the second embodiment is provided for stably holding the substrate sheet while the wiring pattern is scanned as well as for correct positioning of the wiring pattern in relation to the inspection camera 54B.

Fourth Embodiment FIGS. 11A to 11E

Figure 11A:
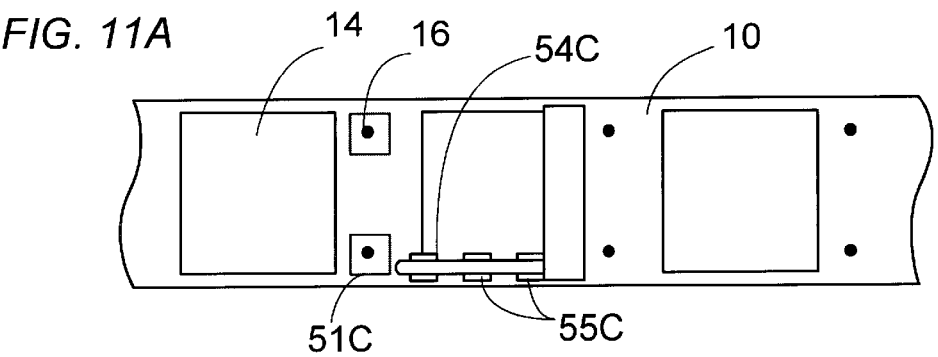
FIGS. 11A to 11E are views for explaining the operation of an inspection system in accordance with a fourth embodiment of the present invention.
Figure 11B:
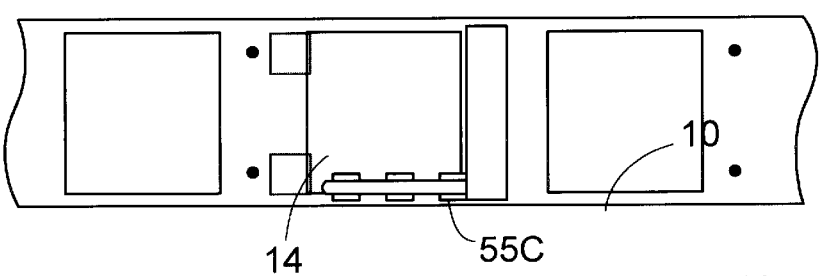
Figure 11C:
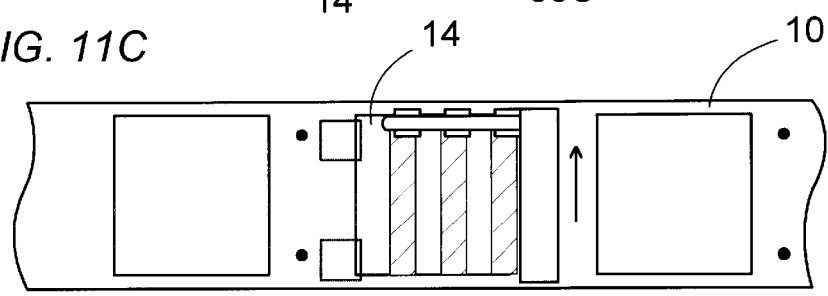
Figure 11D:
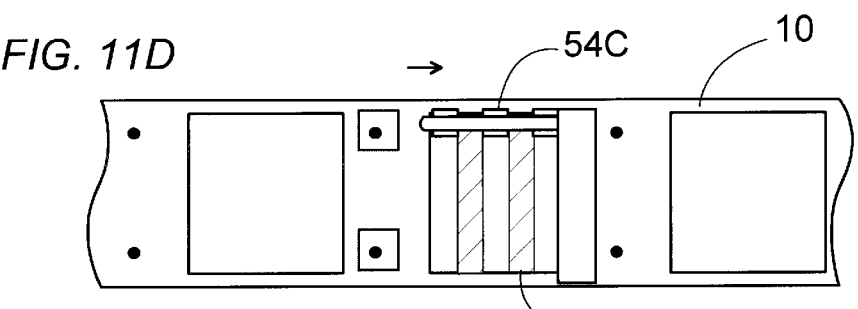
Figure 11E:
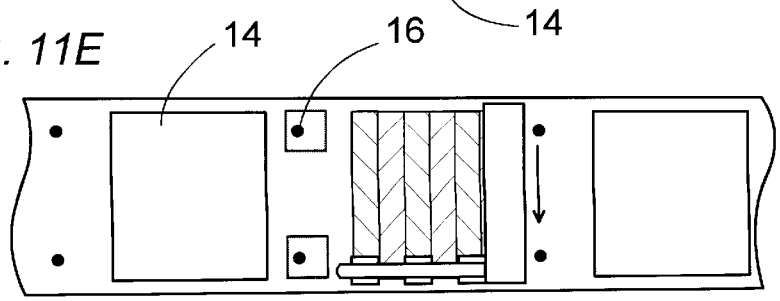

FIGS. 11A to 11E illustrates an inspection system in accordance with a fourth embodiment of the present invention which is similar to the third embodiment except that an inspection camera 54C is composed of separate camera units 55C spaced along the feeding direction of the substrate sheet 10 and is movable in the transverse direction between a first position of FIG. 11A and a second position of FIG. 11C. Like parts are designated by like numerals with a suffix letter of 'C'. The camera units 55C are spaced by a fixed distance such that the entire length of the wiring pattern 14 is covered when the wiring pattern 14 are shifted by that distance in the forward direction. With the use of the inspection camera 54C of this structure, a control is made to feed the substrate sheet 10 by a forward step while reciprocating the inspection camera 54C by one cycle along the transverse direction between the first and second positions. Operation of the system is now discussed. As shown in FIG. 11A, when the wiring pattern 14 proceeds to a pre-inspection position where the corresponding position markings 16 are captured by the position cameras 51C, the controller operates to feed the substrate sheet 10 at a relatively high speed to a first inspection position of FIG. 11B where the leading edge of the wiring pattern 14 is aligned with the forward most inspection camera unit 55C. Then, the inspection camera 54C is caused to shift in the transverse direction by a half-cycle to the position of FIG. 11C with the substrate sheet 10 held stationary for scanning a half area of the wiring pattern (as indicated by hatched lines). Then, the substrate sheet 10 is fed forward by a short distance corresponding the spacing between the adjacent camera units 55C to bring the wiring pattern 14 at a second inspection position of FIG. 11D. Subsequently, the inspect camera 54C is shifted in the reverse direction by the remaining half-cycle to the position of FIG. 11E, thereby completing to scan the whole area of the wiring pattern 14. It is noted that the substrate sheet is fed at a relatively high speed to proceed the wiring pattern 14 from the pre-inspection position of FIG. 11A to the first inspection position of FIG. 11B, while it is fed at a relatively low speed to proceed the wiring pattern from the first inspection position of FIG. 11C to the second inspection position of FIG. 11D, in order to reduce a total inspection time of consecutively inspecting the discrete wiring patterns while assuring a reliable inspection of the individual wiring patterns. Also in this embodiment, the position camera 51C serves to realize a correct positioning of the wiring pattern 14 when it comes to the first inspection position with the control of shifting the feeder and/or the collector in the transverse direction as discussed in the first embodiment. The suction table as discussed with reference to FIGS. 8A and 9A may be applicable to the present system for the same purpose of assuring the reliable inspection.

Figure 12:
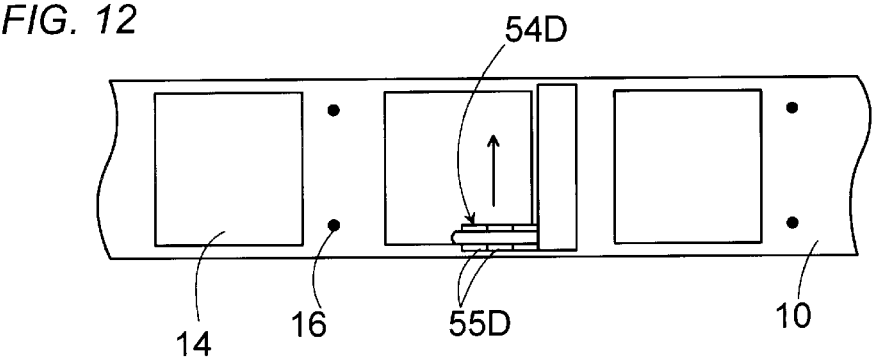
FIG. 12 is a schematic view of a modification of the fourth embodiment.

FIG. 12 illustrates a modification of the third embodiment in which the inspection camera 54D is composed of an array of closely arranged camera units 55D to cover a half length of the wiring pattern 14. The scanning of the wiring pattern 14 can be made by the same sequence as discussed with reference to FIGS. 11A to 11E of the third embodiment.

Figure 13:
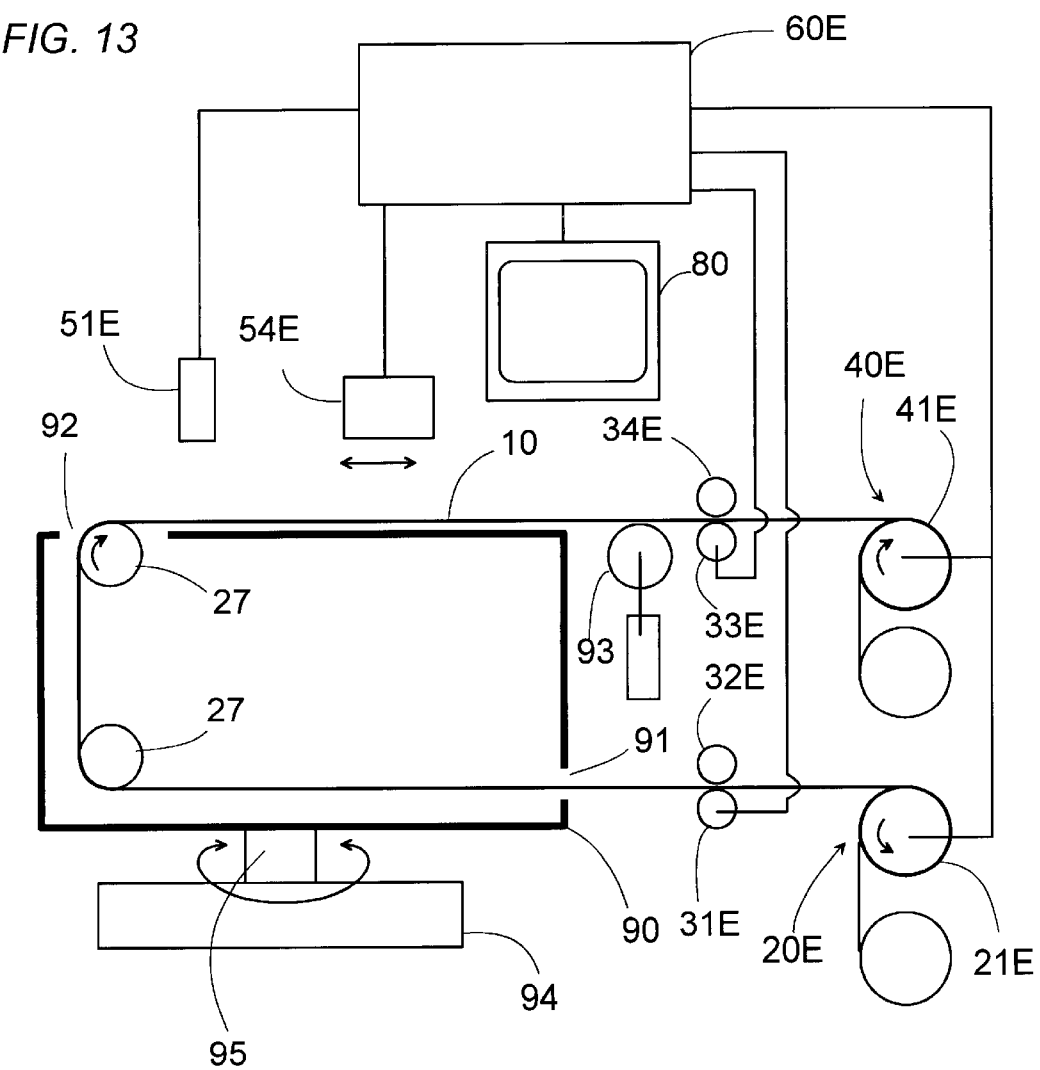
FIG. 13 is a schematic view of an inspection system in accordance with a fifth embodiment of the present invention.

Fifth Embodiment FIG. 13

Referring to FIG. 13, there is shown an inspection system in accordance with a fifth embodiment of the present invention. The inspection system includes a display 80 for re-inspection by human eyes of the wiring pattern determined to be defective by the image processing as explained with the previous embodiments. The system further includes a backup table 90 which passes the substrate sheet 10 thereon and serves as a supporting desk when a personnel requires to apply a force to the wiring pattern being monitored by the display in order to, for example, mend a defective portion with a hand-tool. The basic structure of the system comprises a feeder 20E of feeding the substrate sheet 10 from an unwinder 21E to an inspection zone 30E and a collector 40E of collecting the substrate sheet on a winder 41E. A tension is given to the substrate sheet 10 between a draw-in roller set and a draw-out roller so as to extend the substrate sheet 10 horizontally in the inspection zone 30E. The draw-in roller set is composed of a drive roller 31E and a pinch roller 32E, while the draw-out roller set is likewise composed of a drive roller 33E and a pinch roller 34E. Dispose between the draw-in roller set and the draw-out roller set is a pair of vertically spaced guide rollers 27 by which the feeding direction is reversed. The guide rollers 27 are supported to the backup table 90 and are so positioned to introduce the substrate sheet 10 through an inlet 91 near the bottom of the table and emerge the substrate sheet on top of the table 90 through an outlet 92 at one longitudinal end of the table. Disposed between the table 90 and the draw-out roller set 33E and 34E is a riser roller 93 which is vertically movable in order to lift the substrate sheet 10 up away from the table 90 while feeding the sheet. When the substrate sheet 10 is stopped for inspection of the wiring pattern, the riser roller 93 is lowered to land the sheet on the table 90 for reliable recognition of the defective pattern as well as for facilitating to handle the wiring pattern by the personnel, if needed.

A controller 60E includes a retrieval section which derives from the output of the image processing as made in the previous embodiments that which one or ones of the wiring pattern are determined defective. That is, the identification number assigned to the defective wiring pattern is transmitted to the controller 60E which responds to feed that wiring pattern on the table 90 while passing the non-defective wiring pattern. Local information as to the location of a particular defect found within the area of the wiring pattern is also obtained at the image processing and is fed together with the identification number to the controller 60E such that a television camera 54E is controlled to move to the particular location for giving a magnified image of the defect to the display 80 for easy recognition by the personnel. If the defect is judged to be easily mended, the personnel can make the use of the table 90 as a mending desk to mend the defect with a suitable hand tool.

Like position cameras 51E as utilized in the previous embodiments is mounted to watch the position markings on the substrate sheet 10 and detect a pre-inspection position of the wiring pattern immediately before being inspected by the camera 54E. Based upon the information about the pre-inspection position, the controller 60E instructs to feed the wiring pattern to a correct inspection position, while making suitable correction for possible errors of the lateral shift, directional divergence by moving at least one of the feeder 20E, collector 40E, and table 90 in the transverse direction in the like manner as discussed with reference to the previous embodiments. In this connection, the table 90 is mounted on a foot 94 to be rotatably about a vertical axis of a cylinder 95 such that the table 90 can adjust its orientation in order to compensate for the angular directional divergence of the substrate sheet from an intended feed direction.

Although the position markings are printed separately from the wiring pattern in the aforementioned embodiments, they may be printed within the area of the wiring pattern. Further, the relative position of the separate printed markings to the wiring pattern may be suitably selected in consideration of the particular arrangement of the inspection camera and the other configuration of the system.

What is claimed is:

1. An inspection system for inspecting discrete wiring patterns (14) formed integrally on a continuous substrate sheet (10) of a flexible material, said system comprising:

an inspection zone (30) provided with camera means (51, 54) for inspecting the individual wiring patterns and detecting a position of said wiring pattern on said substrate sheet;

draw-in roller means (31, 32) for introducing the substrate sheet into said inspection zone;

draw-out roller means (33, 34) for drawing out said substrate sheet from said inspection zone, said draw-out roller means being positioned to define said inspection zone between said draw-in roller means and said draw-out roller means and to give a tension to said substrate sheet for extending said substrate sheet straight within said inspection zone;

control means (60) which controls a position of said substrate sheet passing through said inspection zone based upon a position signal detected by said camera means as indicative of said position of said individual wiring patterns on said substrate sheet within said inspection zone;

a feeder (20) for feeding said substrate sheet towards said draw-in roller means from a first stock (21) of said substrate sheet;

a collector (40) for collecting said substrate sheet past through said draw-out roller means into a second stock (41) of said substrate sheet; and a dancer roller (35, 45) being provided at least one of two locations, one between said feeder and said draw-in roller means, and the other between said draw-out roller means and said collector;

wherein said camera means comprises an inspection camera means (54) and a position camera means (51), said inspection camera means (54) providing an image of said wiring pattern to an image inspector (64) where said image is compared with a reference image for determination of a defect in said wiring pattern, said inspection camera means (54) comprising an array of inspection cameras arranged in a direction transverse to a feeding direction of said substrate sheet in such a manner to cover a whole width of said wiring patterns, said position camera means (51) detecting marks (16) on said substrate sheet to acknowledge a pre-inspection position of said wiring pattern which is just before being inspected by said inspection camera and providing said position signal indicative of said pre-inspection position, a speed sensor (35) detecting the feeding speed of said substrate sheet and providing a speed signal indicative of said feeding speed, said control means controlling to feed said substrate through said inspection zone at a uniform speed based upon said speed signal, said control means being responsive to said position signal and said speed signal to activate said inspection camera means (54) for scanning the image of said wiring pattern in synchronism with the position of the wiring patterns.

2. The system as set forth in claim 1, further including
a feeder (20) for feeding said substrate sheet through said draw-in roller means into said inspection zone,
a collector (40) for collecting said substrate sheet past through said draw-out roller means from said inspection zone,
said feeder and said collector being movable in a transverse direction generally perpendicular to a feeding direction of said substrate sheet through said inspection zone,
said control means (60) comprises a mechanism of shifting at least one of said feeder and said collector in said transverse direction, in response to said position signal, for correct positioning of said wiring pattern in said inspection zone.

3. The system as set forth in claim 1, wherein
each of said draw-in and draw-out roller means comprises a driving roller (31, 33) and a pinch roller (32, 34), said driving roller being controlled by said control means to rotate, and said pinch roller pressing said substrate sheet against said driving roller to feed said substrate sheet.

4. The system as set forth in claim 1, wherein
said camera means comprises an inspection camera means (54A) and a position camera means (51A),
said inspection camera means (54A) providing an image of said wiring pattern to an image inspector (64) where said image is compared with a reference image for determination of a defect in said wiring pattern, said position camera means (51A) detecting marks (16) on said substrate sheet (10) to acknowledge a pre-inspection position of said wiring pattern which is just before being inspected by said inspection camera and providing said position signal indicative of said pre-inspection position, said inspection camera means (54A) comprises an array of inspection cameras (55A) arranged in an array direction transverse to a feeding direction of said substrate sheet so as to cover the whole width of said wiring pattern when said array is shifted between a first position and a second position in said array direction, said control means operating to feed said substrate sheet forwardly along said feeding direction by one forward step during which said inspection camera means at said first position completes scanning of a portion of said wiring pattern, and subsequently to feed said substrate sheet reversely by one reverse step during which said inspection camera means at said second position completes scanning of the rest of said wiring pattern.

5. The system as set forth in claim 1, wherein said camera means comprises an inspection camera means (54B) and a position camera means (51B), said inspection camera means (54B) providing an image of said wiring pattern to an image inspector where said image is compared with a reference image for determination of a defect in said wiring pattern, said position camera means (51B) detecting marks (16) on said substrate sheet to acknowledge a pre-inspection position of said wiring pattern which is just before being inspected by said inspection camera means and providing said position signal indicative of said pre-inspection position, said control means operating to intermittently feed said substrate sheet so that said wiring pattern is held stationary at an inspection position for a predetermined period during which said inspection camera means is controlled to move relative to said wiring pattern for inspection of the wiring pattern.

6. The system as set forth in claim 1, wherein said camera means comprises an inspection camera means (54C) and a position camera means (51C), said inspection camera means providing an image of said wiring pattern to an image inspector where said image is compared with a reference image for determination of a defect in said wiring pattern, said position camera means detecting marks (16) on said substrate sheet to acknowledge a pre-inspection position of said wiring pattern which is just before being inspected by said inspection camera means and providing said position signal indicative of said pre-inspection position, said inspection camera means (54C) comprising an array of inspection cameras (55C) arranged in a direction parallel to a feeding direction of said substrate sheet so as to cover the whole width of said wiring pattern when said array reciprocates by one cycle along a transverse direction perpendicular to said feeding direction, said control means operating to hold said substrate sheet at a first inspection position where said inspection camera means is shifted by half of said one cycle in said transverse direction to scan a portion of said wiring pattern, and subsequently feed said substrate sheet by one step to a second inspection position where said inspection camera means is shifted by the remaining half of said one cycle in said transverse direction to scan the rest of said wiring pattern, said control means operating to intermittently feed said substrate sheet so that said wiring pattern is held stationary at said first and second inspection positions at which said inspection camera means is controlled to move relative to said wiring pattern for inspection of the wiring pattern.

7. The system as set forth in claim 1, wherein said camera means comprises a view camera (54E) which gives a selected area of said wiring pattern on a display (80) for inspection by human eyes, said inspection zone being provided with a backup table (90) upon which said substrate sheet being fed.

8. The system as set forth in any one of claims 4 to 6, wherein said inspection zone is provided with a suction table (70) which is positioned behind said substrate sheet to hold said substrate sheet flat on said suction table by a suction force, said suction table being controlled by said control means to hold said substrate sheet while said wiring pattern is being scanned by said inspection camera means and to release said substrate sheet after said wiring pattern is inspected.

9. The system as set forth in claim 8, wherein said suction table (70A) has a feed axis extending along a feeding direction of said substrate sheet and is capable of swinging around a vertical axis perpendicular to a plane of said substrate sheet to adjust an angle of said feed axis with respect to said feeding direction for correct positioning of said wiring pattern in relation to said inspection camera means.

10. The system as set forth in claim 8, wherein said suction table (70) is movable in synchronism with said substrate sheet being fed through said inspection zone.

* * * * *